United States Patent [19]
Hosokawa et al.

[11] 3,995,061
[45] Nov. 30, 1976

[54] PHARMACEUTICAL COMPOSITION AND METHOD OF USING THE SAME
[75] Inventors: Tomoyoshi Hosokawa, Machida; Tsuneo Okutomi, Fujimi; Hiroshi Sasaki, Higashikurume; Kouji Suzuki, Tama; Mikio Sawada, Sayama, all of Japan
[73] Assignee: Chugai Seiyaku Kabushiki Kaisha, Tokyo, Japan
[22] Filed: Mar. 31, 1975
[21] Appl. No.: 563,514

[30] Foreign Application Priority Data
Apr. 9, 1974  Japan.................................. 49-39440

[52] U.S. Cl.............................. 424/331; 260/590 C
[51] Int. Cl.².................... A61K 31/12; C07C 49/76
[58] Field of Search................... 424/331; 260/590 C

[56] References Cited
UNITED STATES PATENTS
3,546,073  12/1970  Evans.................................. 424/331

OTHER PUBLICATIONS
Stedman's Medical Dict., Williams & Wilkins, Balto. 22nd Ed., 1972, pp. 111, 123.

Primary Examiner—Albert T. Meyers
Assistant Examiner—A. P. Fagelson
Attorney, Agent, or Firm—Browdy and Neimark

[57] ABSTRACT

A pharmaceutical composition for treatment of arteriosclerosis of mammals, including human beings, and poultry which comprises an ascochlorin derivative represented by the formula

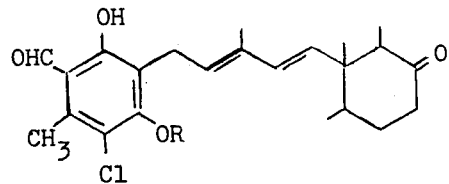

and a pharmaceutically acceptable carrier and a method for treating arteriosclerosis by the use of the composition above is disclosed.

10 Claims, 2 Drawing Figures

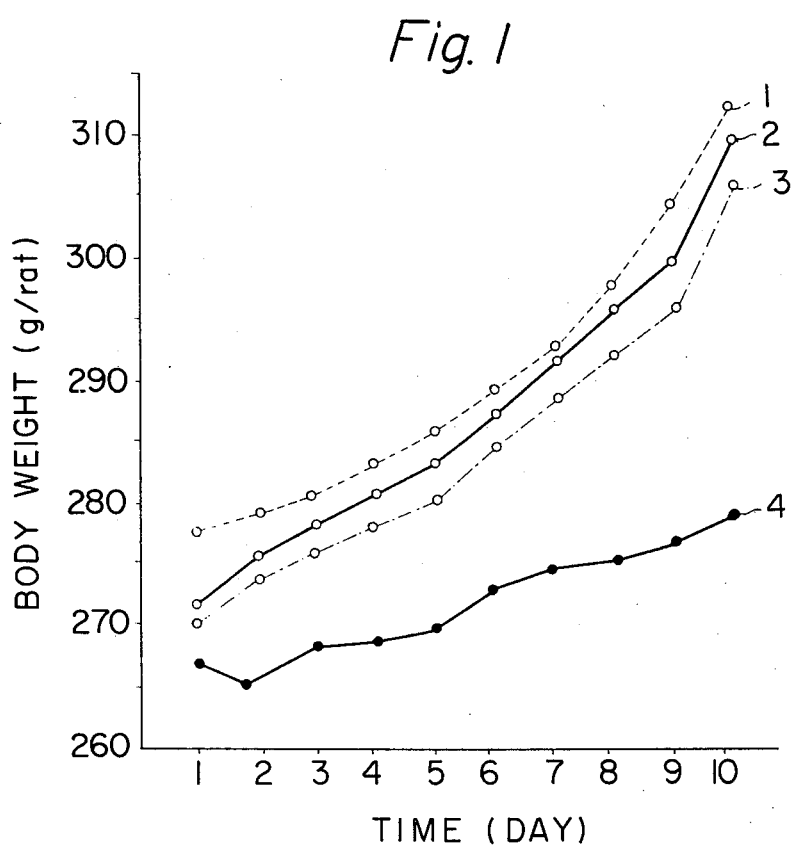

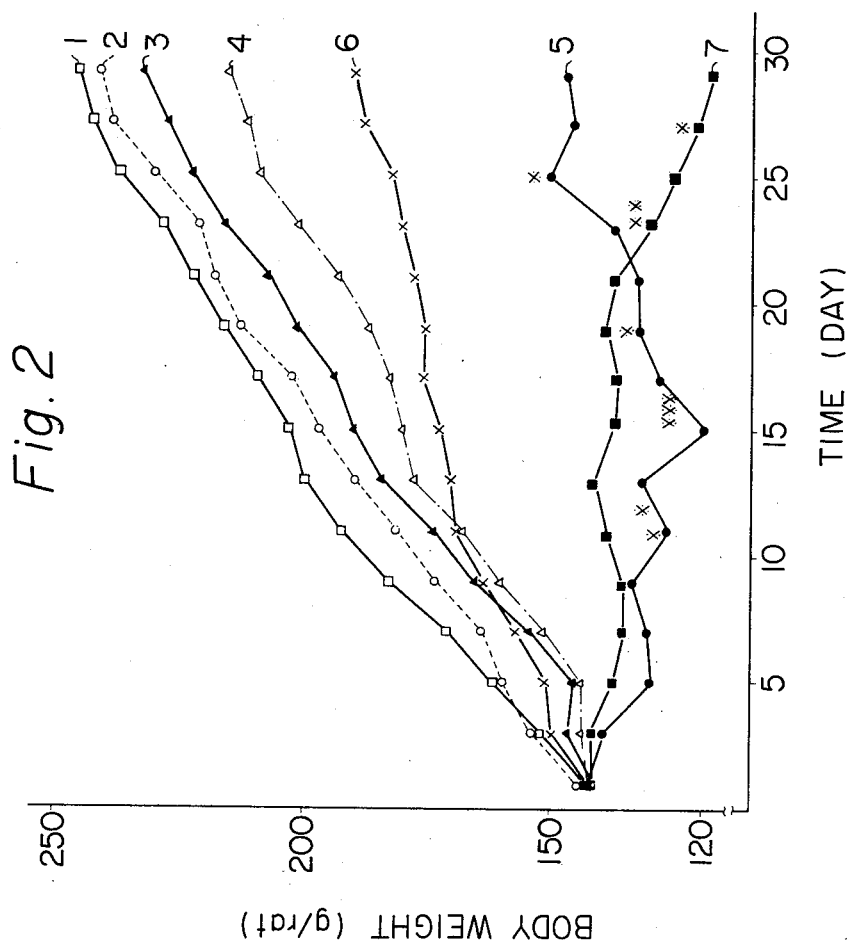

PHARMACEUTICAL COMPOSITION AND METHOD OF USING THE SAME

This invention relates to a pharmaceutical composition for treatment of arteriosclerosis of mammals, including human beings, and poultry and a method for using such a composition. Particularly, it relates to a pharmaceutical composition for treatment of arteriosclerosis of mammals, including human beings, and poultry containing an ascochlorin derivative as an effective ingredient, and also to a method for using said composition.

It is known that, among various causes of death, the proportion of deaths in human beings due to diseases caused by arteriosclerosis is high. Although the cause of arteriosclerosis is not fully understood, it is generally supposed that hyperlipemia caused by excessive intake of lipid and/or hereditary factors accelerates the arterio deposition of lipid and consequently, atheromatosis is revealed on the wall of arteries.

Further, it is also known that direct cause of death in arteriosclerosis patients is mainly due to the formation in arteries of white thrombus comprising blood platelets and fibrin.

One object of this invention is to provide a pharmaceutical composition for treatment of arteriosclerosis of mammals, including human beings, and poultry having hypolipidemic activity together with blood platelet anti-aggregation activity.

Another object of this invention is to provide a method for treating arteriosclerosis of mammals, including human beings, and poultry by the use of said pharmaceutical composition.

Other objects will be self-evident from the description hereinbelow.

Ascochlorin is an antibiotic substance which is produced from a filamentous fungus such as *Ascochyta viciae Libert* (deposited in the culture collection of the Agency of Industrial Science and Technology, Fermentation Research Institute, Japan under deposit number FERM-P No. 129) and has the following formula:

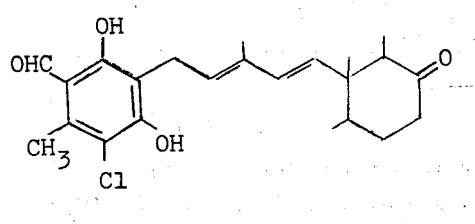

The antibiotic is known to have anti-viral, anti-tumor, anti-bacterial and sedative activities and, further, cholesterol-lowering activity. The anti-viral and anti-tumor activities of the antibiotic are known from Japanese Patent No. 585,252 and anti-bacterial, sedative and cholesterol-lowering activities are disclosed in U.S. Pat. No. 3,546,073. However, this antibiotic is inadequate in its hypolipidemic activity, it is also strong in toxicity; its toxicity is especially noticeable when continuously administered.

The inventors of this invention had prepared a number of ascochlorin derivatives, tested them for their hypolipidemic activity and toxicity and finally found some derivatives suitable for the purpose of this invention which are represented by the formula

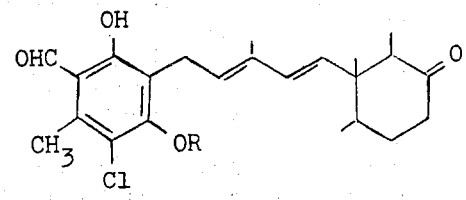

wherein R is an alkyl radical having 1–4 carbon atoms. The derivatives have excellent hypolipidemic activity, including cholesterol-lowering activity and blood platelet anti-aggregation activity and, also, they are low in toxicity. The inventors then continued their experiments on the derivatives to complete the present invention.

FIG. 1 is a graph showing the increase in body weight of rats to which 4-O-methylascochlorin or ascochlorin was administered every day for 10 days. In FIG. 1, Curve 1 corresponds to the control group (no medication); Curve 2 corresponds to the group which received 4-O-methylascochlorin in a dose of 10 mg/head per day; Curve 3 corresponds to the group which received 4-O-methylascochlorin in a dose of 20 mg/kg per day; and Curve 4 corresponds to the group which received with ascochlorin in a dose of 10 mg/kg per day.

FIG. 2 is a graph showing the increase in body weight of rats receiving 4-O-methylascochlorin, ascochlorin or ethyl-α-(p-chlorophenoxy) isobutylate every day for 30 days. In the Figure, Curve 1 corresponds to the control group (no medication); Curve 2,3,4 and 5 correspond to the groups received 4-O-methylascochlorin in a dose of each of 250, 500, 1,000, 2,000 mg/kg/day, respectively; Curve 6 corresponds to the Group received ethyl-α-(p-chlorophenoxy) isobutylate in a dose of 500 mg/kg/day; Curve 7 corresponds to the group received ascochlorin in a dose of 50 mg/kg/day; and symbol ✕ shows a rat died.

One embodiment of this invention is a pharmaceutical composition for treatment of arteriosclerosis of mammals, including human beings, and poultry which comprises, as an effective ingredient, an ascochlorin derivative represented by the formula

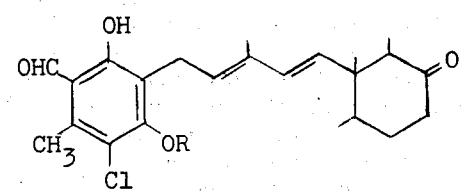

wherein R is an alkyl radical having 1–4 carbon atoms, in an amount sufficient to exhibit desired effect.

The derivatives represented by the general formula disclosed above include 4-O-methylascochlorin, 4-O-ethylascochlorin, 4-O-n-propylascochlorin, 4-O-isopropylascochlorin, 4-O-n-butylascochlorin, 4-O-isobutylascochlorin, 4-O-sec-butylascochlorin and 4-O-tertbutylascochlorin, among them 4-O-methylascochlorin being a known compound while the compounds other than 4-O-methylascochlorin are novel. These novel compounds may be prepared from ascochlorin by, for example, selectively alkylating a hydroxyl radical of 4-position of the compound in the presence of a basic condensing agent.

Because the ascochlorin derivatives are almost insoluble in water, they may be suspended in an aqueous solution of gum arabic, sucrose, etc. to form a suspension and moreover they may be formulated by a conventional way with a conventional, pharmaceutically acceptable carrier such as lactose, starch, crystalline cellulose, kaolin, calcium carbonate, talc and the like to form tablets, granules or powder. Further, the resulting granules or powder may be stuffed in capsules to form capsules.

Although the amount of the ascochlorin derivative in the composition depends on the kind of animal to which it is to be administered or the form of the composition, it is an amount such that the use of the composition realizes the administration of the derivative in an amount of usually 0.05–500, preferably 0.5–50 mg/kg.body weight per day, because the ascochlorin derivative reveals the effect by continuous oral administration in a dose of 0.05 mg/kg.body weight per day for several days. Other one or more medicines known to be effective in treating arteriosclerosis, for example, ethyl-α-(p-chlorophenoxy) isobutylate, dextran sulfate, nicotinic acid derivatives, dipyridamol and the like, may also be incorporated in the composition.

Another embodiment of this invention is a method for treating arteriosclerosis of mammals, including human beings, and poultry which comprises administering the pharmaceutical composition containing the ascochlorin derivative of this invention to an animal.

In order to treat arteriosclerosis by the use of the composition prepared according to the present invention, mammals and poultry are orally administered with the pharmaceutical composition prepared according to the present invention once or more a day. Especially, for human beings, it is preferable to administer the composition three times per day, after every meal. For animals other than human beings, the composition may be administered alone or by mixing it with feed. As stated above, the dose of the composition depends on the kind of animals to which it is to be administered and on the form of the composition. However, the dose ranges generally 0.05–500, preferably 0.5–50 mg/kg.body weight per day based on the ascochlorin derivative. For human beings, although the study has not been completed, a satisfactory effect was obtained by the oral administration of a 50 mg dose after every meal when 4-O-methylascochlorin was used.

The mammals and poultry, arteriosclerosis of which can be treated by the administration of the composition of this invention include, for example, human beings, monkeys, bovines, dogs, cats, pigs and chickens.

This invention is further explained by specific Examples and Experiments hereinbelow. However, it should be understood that the Examples and Experiments do not limit this invention.

PREPARATION OF ASCOCHLORIN DERIVATIVES

Ascochlorin (404 mg) was dissolved in acetone (5 ml) followed by adding potassium carbonate (150 mg) and ethyl iodide (0.2 ml). The solution was stirred in reflux for 2 hours, and after the completion of the reaction, the mixture was cooled and filtered to remove potassium carbonate, and then acetone was evaporated off. Water was added to the residue and extracted with ether. The extract was washed several times with an aqueous solution of sodium bicarbonate and a diluted hydrochloric acid, then dried over sodium sulfate and concentrated. The resulting residue was crystallized from methanol-hexane to obtain 390 mg of 4-O-ethylascochlorin as needles. (m.p. 134.5° C)

Elemental Analysis: Calc. for $C_{25}H_{33}ClO_4$: C, 69.36; H, 7.63; Cl, 8.21 (%). Found: C, 69.09; H, 7.68; Cl, 8.16 (%).

By the way similar to that described above, 4-O-n-propylascochlorin, 4-O-isopropylascochlorin, 4-O-n-butylascochlorin, 4-O-isobutylascochlorin, 4-O-sec-butylascochlorin and 4-O-tert-buthylascochlorin were prepared.

EXAMPLE 1

Serum cholesterol lowering activity

The cholesterol lowering activity of the ascochlorin derivatives of this invention was observed by the use of Wister-Imamich strain male rats weighing 230 ± 30 g which had been bred with the use of high-fat feed comprising 1000 g of powdery chow CLEA CE-2 (sold by NIHON CLEA KABUSHIKI KAISHA) admixed with 10 g of cholesterol, 95 g of hydrogenated coconut oil, 2 g of cholic acid, 150 g of milk casein and 671 g of sucrose.

The rats were divided into groups of five members each, and orally administered with a different ascochlorin derivative as a suspension in gum arabic aqueous solution in a dose of 75 mg/kg.body weight. The rats were kept from eating food, and 6 hours after the administration, the blood of each rat was sampled from its heart. The total amount of cholesterol in serum was determined by a modified Zurkowski method (Clinical Chemistry, 10, 451, 1964) with the use of a colorimeter for blood analysis (sold by KYOTO DAIICHI KAGAKU). The results are shown in Table I below.

Table I

| Test Compound | Cholesterol in serum (mg/dl) | Drop Ratio |
|---|---|---|
| 4-O-methylascochlorin | 76.6 | −22.8 |
| 4-O-ethylascochlorin | 82.2 | −17.2 |
| 4-O-n-propylascochlorin | 84.3 | −15.1 |
| 4-O-isopropylascochlorin | 85.6 | −13.8 |
| 4-O-n-butylascochlorin | 86.9 | −12.5 |
| 4-O-sec-butylascochlorin | 89.1 | −10.3 |
| 4-O-isobutylascochlorin | 88.5 | −10.9 |
| 4-O-tert-butylascochlorin | 82.7 | −16.7 |
| Control (ascochlorin) | 101.3 | +2.0 |
| Control (ethyl-α-(p-chlorophenoxy) isobutylate) | 103.8 | +4.5 |
| Control (gum arabic aqueous solution only) | 99.3 | — |

EXAMPLE 2

Aggregation inhibition acitivity of blood platelet

In this Example Wister-Imamich strain male rats weighing 230 ± 30 g which had been bred with the use of a commercial chow, CLEA CE-2 were used.

The rats were divided into groups of five members each, and orally administered with a different ascochlorin derivative as a suspension in 2% gum arabic aqueous solution in a dose of 20 mg/kg.body weight. Six hours after the administration, the blood of each rat was sampled from the heart and after the addition of citric acid, the blood sample was centrifuged at 1,500 r.p.m. for 10 minutes to obtain platelet rich plasma. The anti-aggregation effect when the concentration of adenosine-5'-diphosphate in the platelet rich plasma is ultimately $10^{-5}M$ is shown in Table II.

As positive controls, ascochlorin, ethyl-α-(p-chlorophenoxy) isobutylate and acetyl salicyclic acid were used. The aggregation inhibition ratio was evaluated in percent by comparing the increase of transmission rate caused by the addition of adenosin-5'-diphosphate to platelet rich plasma of the control group (no medication) with that caused on the groups administered with an ascochlorin derivative which is calculated for 100.

Table II

| Test Compound | Aggregation Inhibition Ratio (%) |
|---|---|
| 4-O-methylascochlorin | 70.5 |
| 4-O-ethylascochlorin | 55.3 |
| 4-O-n-propylascochlorin | 56.5 |
| 4-O-isopropylascochlorin | 57.2 |
| 4-O-n-butylascochlorin | 53.7 |
| 4-O-sec-butylascochlorin | 51.1 |
| 4-O-isobutylascochlorin | 48.8 |
| 4-O-tert-butylascochlorin | 60.5 |
| Control (ascochlorin) | 66.8 |
| Control (ethyl-α-(p-chlorophenoxy) isobutylate) | 0 |
| Control (acetyl salicylic acid) | 73.1 |

EXAMPLE 3

Toxicity Test a. Acute toxicity

Acute toxicity of the ascochlorin derivatives was observed by the use of Wister-Imamichi strain male rats weighing 230 ± 30 g and ddY strain male and female mice (5 weeks old) weighing 20 ±3 g which were divided into groups of 10 members each. Japanese native male rabbits weighing 2 kg ± 300 g which were divided into groups of five members each were also used. The test animals were orally or intraperitoneally administered with a different ascochlorin derivative as a suspension in 5% gum arabic aqueous solution, and the toxicity was compared with that of control in which ascochlorin was used. The results are shown in Table III below.

Table III

| Test Compound | Test Animal | Sex | Administration Route | $LD_{50}$ (mg/kg) |
|---|---|---|---|---|
| Ascochlorin | Mouse | Male | Oral | >5,000 |
| " | " | Female | " | >5,000 |
| " | " | Male | i.p.* | 102 (57–184) |
| " | " | Female | " | 68 (35–133) |
| " | Rat | Male | Oral | >7,000 |
| " | " | " | i.p. | 258 (156–426) |
| 4-O-methylascochlorin | Mouse | Male | Oral | >7,300 |
| " | " | Female | " | >7,300 |
| " | " | Male | i.p. | 5,000 |
| " | " | Female | " | 5,500 |
| " | Rat | Male | Oral | >10,000 |
| " | " | " | i.p. | 3,100 |
| " | Rabbit | Male | Oral | >2,000 |
| 4-O-ethylascochlorin | Mouse | " | i.p. | 5,600 |
| " | Rat | " | " | 5,100 |

*i.p.: intraperitoneal b. Toxicity by continuous administration for 10 days.

Wister-Imamichi strain male rats weighing 230 ± 30 g were divided into four groups of 10 members each, 3 groups of which were orally administered with 4-O-methylascochlorin in a dose of 10 mg/head, 4-O-methylascochlorin in 20 mg/head and ascochlorin in 10 mg/head, respectively, as a suspension in 2% gum arabic aqueous solution once a day for 10 days. The remaining group was administered with 2% gum arabic aqueous solution, the dose and way of administration being identical to those disclosed above. The increase in body weight of the rats of each group was observed every day during the administration. The results are shown in the graph of FIG. 1.

FIG. 1 clearly shows that the group to which ascochlorin was administered in a dose of 10 mg/head increased only slightly in body weight, while the group receiving 4-O-methylascochlorin had a normal increase in body weight almost comparable to that of the control group receiving only gum arabic aqueous solution. The tendency shown above was observed in the cases of 4-O-ethylascochlorin, 4-O-n-propylascochlorin, 4-O-isopropylascochlorin, 4-O-n-butylascochlorin, 4-O-sec-butylascochlorin and 4-O-tert-butylascochlorin.

c. Toxicity by continuous administration for 30 days

Wister strain male rats weighing 150 ± 20 g were divided into groups of 10 members each, and each group was orally administered with 4-O-methylascochlorin as a suspension in 2% gum arabic aqueous solution in a predetermined dose once a day for 30 days, and the increase in body weight thereof was observed each day that the administration continued. As controls, ascochlorin (50 mg/kg/day) and ethyl-α-(p-chlorophenoxy) isobutylate (500 mg/kg/day) were used. The results are shown in the graph in FIG. 2.

The groups receiving 4-O-methylascochlorin in a dose of 250 and 500 mg/kg exhibited normal increase in body weight comparative to the untreated group. In contrast, little or no increase in body weight was observed in the group receiving ascochlorin in a dose of 50 mg/kg, and moreover they lost weight. The three rats of the group died during the test period.

EXAMPLE 4

Hypolipidemic activity of 4-O-methylascochlorin in blood and in organs

Wister strain rats weighing 150 ± 20 g were divided into groups of 10 members each and bred with high-fat feed, the same as that used in Example 1.

The rats were orally administered ascochlorin, 4-O-methylascochlorin or ethyl-α-(p-chlorophenoxy) isobutylate in a predetermined dose every morning for 30 days. Six hours after the last administration, liver and aorta of each rat were taken out and lipid level in the organs of each of the rats were determined. Lipid present in the liver and aorta was extracted with methanol-chloroform (1:1) by allowing it to stand overnight and the extract was assayed as to lipid level. The results obtained are shown in Tables IV and V below.

Table IV

| Test Compound | Dose (mg/kg) | Change in Level of Serum Lipid ||||| 
|---|---|---|---|---|---|---|
| | | Cholesterol (mg/dl) | Triglyceride (mg/dl) | Phospholipid (mg/dl) | Free fatty acid (μ eq./dl) | β-Lipoprotein (mg/dl) |
| Ascochlorin | 10.0 | 97.4±4.8 (−8.8) | 72.0±13.2 (−10.0) | 130.1±8.4 (−4.5) | 48.3±4.7 (−4.0) | 720±114 (−5.6) |
| 4-O-methylascochlorin | 2.25 | 102.4±13.8 (−4.2) | 74.5±9.8 (−6.8) | 119.7±12.5 (−12.2) | 49.1±8.2 (−2.4) | 819±109 (+7.3) |
| | 9.0 | 87.0±4.9 (−18.6) | 64.8±5.2 (−19.0) | 118.4±5.8 (−13.2) | 44.8±3.5 (−10.4) | 593±85 (−22.3) |

Table IV-continued

| Test Compound | Dose (mg/kg) | Change in Level of Serum Lipid | | | | |
|---|---|---|---|---|---|---|
| | | Cholesterol (mg/dl) | Triglyceride (mg/dl) | Phospholipid (mg/dl) | Free fatty acid ($\mu$ eq./dl) | $\beta$-Lipoprotein (mg/dl) |
| | 22.5 | 88.8±9.1 (−16.9) | 63.6±4.6 (−20.5) | 117.9±6.5 (−13.5) | 42.1±2.7 (−16.3) | 589±133 (−22.8) |
| Ethyl-α-(p-chlorophenoxy) isobutylate | 45.0 | 115.3±5.5 (+7.9) | 72.1±4.4 (−9.2) | 135.9±13.6 (−0.7) | 45.2±1.6 (−10.1) | 738±46 (−3.7) |
| Control | — | 106.8±9.7 | 80.0±9.3 | 136.3±4.8 | 50.3±4.3 | 763±126 |

Remarks:
FIGS. in the Table show average value and standard error.
FIGS. in parentheses indicate increasing or reducing ratio based on the control.

Table V

| Test Compound | Dose (mg/kg) | Change of Lipid Level in Organs and Aorta Abdominalis | | | |
|---|---|---|---|---|---|
| | | Cholesterol in Liver (mg/g) | Triglyceride in Liver (mg/g) | Phospholipid in Liver (mg/g) | Cholesterol in Tunica intima of aorta abdominalis (δ/mg) |
| Ascochlorin | 10.0 | 36.2±3.5 (+6.5) | 20.2±2.5 (−7.3) | 69.5±4.2 (−1.0) | 10.0±0.8 (−4.0) |
| 4-O-methylascochlorin | 2.25 | 38.4±6.4 (+12.9) | 16.7±1.3 (−23.6) | 72.0±5.3 (+2.6) | 18.2±1.4 (−8.1) |
| | 9.0 | 28.9±3.6 (−15.0) | 17.2±2.8 (−21.1) | 69.1±9.9 (−1.6) | 14.0±0.3 (−29.3) |
| | 22.5 | 26.6±2.2 (−21.8) | 17.0±0.7 (−22.1) | 61.8±4.3 (−12.0) | 13.3±0.4 (−32.8) |
| Ethyl-α-(p-chlorophenoxy) isobutylate | 45.0 | 41.0±4.5 (+20.6) | 24.2±2.2 (+10.7) | 79.5±3.1 (+13.2) | 16.9±1.4 (−14.7) |
| Control | — | 34.0±5.4 | 21.8±3.4 | 70.2±3.4 | 19.8±1.0 |

Remarks:
FIGS. in the Table show average value and standard error.
FIGS. in parentheses indicate increasing or reducing ratio based on the control.

As shown in Tables IV and V, in those cases in which 4-O-methylascochlorin was administered in a dose of 9 mg/kg or more, the levels of all types of lipids were extremely lowered and besides, the amount of lipids in liver and cholesterol in aorta was also remarkably reduced. In contrast, such effects were not observed in the groups receiving ascochlorin or ethyl-α-(p-chlorophenoxy) isobutylate.

EXAMPLE 5

Pharmaceutical preparation a. Capsules

To 100 g of pulverized 4-O-methylascochlorin were added 358 g of lactose and 2 g of magnesium stearate and they were thoroughly mixed, and hard gelatin capsules each weighing 65 mg were filled with 230 mg each of the mixture to form capsules.

b. Powder

To 50 g of pulverized 4-O-methylascochlorin were added 404 g of lactose, 45 g of crystalline cellulose and 1 g of magnesium stearate and they were thoroughly mixed to form powder.

c. Tablet-I

To 100 g of pulverized 4-O-methylascochlorin were added 210 g of lactose, 72 g of microcrystalline cellulose, 14 g of corn starch and 4 g of magnesium stearate and they were thoroughly mixed; then, with a tablet machine the mixture was formed into tablets each tablet being 8 mm in diameter and 200 mg in weight.

d. Tablet-II

After being passed through a screen of 50 mesh (Tyler), 100 g of pulverized 4-O-methylascochlorin was mixed with 273 g of lactose and 20 g of calcium carboxymethyl cellulose, and then the mixture was kneaded with a starch paste made of 4 g of corn starch and water. The resulting mixture was granulated by a granulating machine and dried and the granules were passed through a screen of 14 mesh (Tyler). After addition of and mixing with 3 g of magnesium stearate, the mixture was formed into tablets, each being 8 mm in diameter and 200 mg in weight.

e. Suspension

To 400 ml of solution of 200 g of sucrose in water were added 10 g of crystalline cellulose and 0.75 g of sodium carboxymethyl cellulose to form a uniform suspension. Separately, 5 g of bulk of 4-O-methylascochlorin was pulverized in a ball mill together with 0.5 g of a fatty acid ester of sucrose and 20 ml of water. To the resulting powder was added the suspension followed by water to make the total amount 500 ml. The suspension was stirred to form a uniform suspension.

What is claimed is:

1. A pharmaceutical composition for treatment of arteriosclerosis of mammals and poultry which comprises, as an effective ingredient, an ascochlorin derivative represented by the formula

[Chemical structure: benzene ring with OH, OHC, CH₃, Cl, OR substituents, connected via a diene chain to a cyclohexanone ring]

wherein R is an alkyl radical having 1–4 carbon atoms in an amount sufficient to exhibit treatment of arteriosclerosis and a pharmaceutically acceptable carrier.

2. A pharmaceutical composition as set forth in claim 1 wherein said composition is a pharmaceutical composition for treatment of arteriosclerosis of human beings.

3. A pharmaceutical composition as set forth in claim 1 wherein said composition is a pharmaceutical composition for treatment of arteriosclerosis of monkeys, bovines, dogs, cats, pigs and chickens.

4. A pharmaceutical composition for treatment pf arteriosclerosis of mammals and poultry as set forth in claim 1 wherein said ascochlorin derivative is 4-O-methylascochlorin.

5. A pharmaceutical composition for treatment of arteriosclerosis of mammals and poultry as set forth in claim 1 wherein the form of said composition is suspension, tablet, granule, powder or capsule.

6. A method for treating arteriosclerosis of mammals and poultry which comprises orally administering thereto a pharmaceutical composition comprising, as the effective ingredient, an ascochlorin derivative represented by the formula

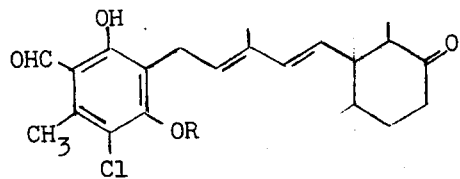

wherein R is an alkyl radical having 1–4 carbon atoms and a pharmaceutically acceptable carrier wherein said derivative is administered to the animal in an amount of 0.05–500 mg/kg.body weight per day in terms of the effective ingredient.

7. A method for treating arteriosclerosis of mammals and poultry as set forth in claim 6 wherein the dose of said pharmaceutical composition is 0.5-50 mg/kg.body weight per day in terms of the effective ingredient.

8. A method for treating arteriosclerosis as set forth in claim 6 wherein the mammals to which said composition is to be administered are human beings.

9. A method for treating arteriosclerosis as set forth in claim 6 wherein the mammals and poultry to which said compositions is to be administered are monkeys, bovines, dogs, cats, pigs and chickens.

10. A method for treating arteriosclerosis as set forth in claim 6 wherein said ascochlorin derivative is 4-O-methylascochlorin.

* * * * *

UNITED STATES PATENT AND TRADEMARK OFFICE
CERTIFICATE OF CORRECTION

PATENT NO. : 3,995,061
DATED : November 30, 1976
INVENTOR(S) : HOSOKAWA et al

It is certified that error appears in the above-identified patent and that said Letters Patent are hereby corrected as shown below:

Column 8, Table V, last column, line 6, "10.0±0.8" should read -- 19.0±0.8 --

Column 8, Claim 4, line 1, "pf" should read --of--

Signed and Sealed this

Thirty-first Day of May 1977

[SEAL]

Attest:

RUTH C. MASON
Attesting Officer

C. MARSHALL DANN
Commissioner of Patents and Trademarks

UNITED STATES PATENT OFFICE
CERTIFICATE OF CORRECTION

Patent No. 3,995,061          Dated November 30, 1976

Inventor(s) Hosokawa, et al

It is certified that error appears in the above-identified patent and that said Letters Patent are hereby corrected as shown below:

Column 8, Table V, last column, line 5, "($\delta$/mg)" should read --($\gamma$/mg)--.

Signed and Sealed this

Twentieth Day of September 1977

[SEAL]

Attest:

RUTH C. MASON  
Attesting Officer

LUTRELLE F. PARKER  
Acting Commissioner of Patents and Trademarks